United States Patent [19]

Mori

[11] Patent Number: 4,790,500
[45] Date of Patent: Dec. 13, 1988

[54] OPTICAL CONDUCTOR CABLE SUPPORTING STAND FOR A LIGHT RAY RADIATION DEVICE USED IN MEDICAL TREATMENT

[76] Inventor: Kei Mori, 3-16-3-501, Kaminoge, Setagaya-ku, Tokyo, Japan

[21] Appl. No.: 81,044

[22] Filed: Aug. 3, 1987

[30] Foreign Application Priority Data

Aug. 26, 1986 [JP] Japan .................................. 61-199737

[51] Int. Cl.⁴ .............................................. F16L 3/00
[52] U.S. Cl. ........................................ 248/49; 248/59; 248/65; 248/80; 248/157; 248/296
[58] Field of Search ................. 248/49, 59, 65, 73, 248/74.1, 79, 80, 157, 161, 176, 124, 218.4, 219.4, 220.2, 229, 230, 231.5, 285, 296, 298, 419; 403/396, 399, 385, 388

[56] References Cited

U.S. PATENT DOCUMENTS

| | | | |
|---|---|---|---|
| 1,375,888 | 4/1921 | Baer | 248/296 X |
| 2,767,003 | 10/1956 | Gilmont | 248/124 X |
| 2,958,110 | 11/1960 | McBrien | 248/124 X |
| 3,223,826 | 12/1965 | Macaluso, Jr. | 248/124 X |
| 4,017,046 | 4/1977 | Hicks | 248/49 X |
| 4,064,737 | 12/1977 | Sieverin | 248/124 X |
| 4,115,966 | 9/1978 | DeLee | 403/385 X |
| 4,321,917 | 3/1982 | Campbell | 248/124 X |

FOREIGN PATENT DOCUMENTS

0819318 9/1959 United Kingdom ................ 248/124

*Primary Examiner*—Ramon O. Ramirez
*Attorney, Agent, or Firm*—Jordan and Hamburg

[57] ABSTRACT

A light ray radiation device for use in medical treatment having optical conductor cables which transmit light rays corresponding to the visible light ray components of solar rays needs an optical conductor cable supporting stand. The stand comprises an upright pole fixedly mounted on a fixing pedestal, a supporting fixture slidably and rotatably attached to the upright pole, a supporting arm fixed the supporting fixture and perpendicular the upright pole, and fixedly mounted members which are slidably and rotatably mounted onto the supporting arm. The fixedly mounted members being comprised of cable receiving portions unitarily attached thereto which intersect the supporting arm and support the optical conductor cables.

12 Claims, 3 Drawing Sheets

OPTICAL CONDUCTOR CABLE SUPPORTING STAND FOR A LIGHT RAY RADIATION DEVICE USED IN MEDICAL TREATMENT

BACKGROUND OF THE INVENTION

The present invention relates to an optical conductor cable supporting stand capable of stably holding optical conductor cables which transmit light rays corresponding to visible light ray components of the sun in order to radiate the light rays onto a diseased part of a patient as a form of medical treatment.

In recent years, a large number of persons suffer from incurable diseases such as arthritis, neuralgia and rheumatism, from pain of an injury scar or a bone fracture, or from pain of an ill-defined disease. Furthermore, persons cannot avoid growing-old and of one's skin showing signs of age progressing gradually from a comparatively young age.

The present applicant has previously proposed a light ray radiating device for use in medical treatment which focuses solar rays or artificial light rays by the use of lenses or the like, and guides the same into an optical conductor, and transmits them onto an optional desired place through the optical conductor. And further, the present applicant has found that visible light rays not containing ultraviolet rays, infrared rays, etc. promote a living body reaction, and thereby the same promotes the health of a person or prevents the person's skin from appearing to grow old, and furthermore, those visible light rays have the noticeable effect of curing arthritis, neuralgia, bedsores, rheumatism, injuries, bone fractures, and the like, and of stopping pain from those diseases.

SUMMARY OF THE INVENTION

The primary object of the present invention is to provide an optical conductor cable supporting stand capable of stably holding the optical conductor cables used in transmitting light rays corresponding to the visible light ray components of the sun and thereby rapidly and adequately radiating the light rays onto a diseased part of a patient as a form of medical treatment.

It is another object of the present invention to provide an optical conductor cable supporting stand capable of stably, rapidly and easily positioning and removing the optical conductor cable.

It is another object of the present invention to provide an optical conductor cable supporting stand capable of fine adjustment of the cable position.

The above-mentioned features and other advantages of the present invention will be apparent from the following detailed description which goes with the accompanying drawings.

DESCRIPTION OF THE PREFERRED EMBODIMENTS

Figure 1:
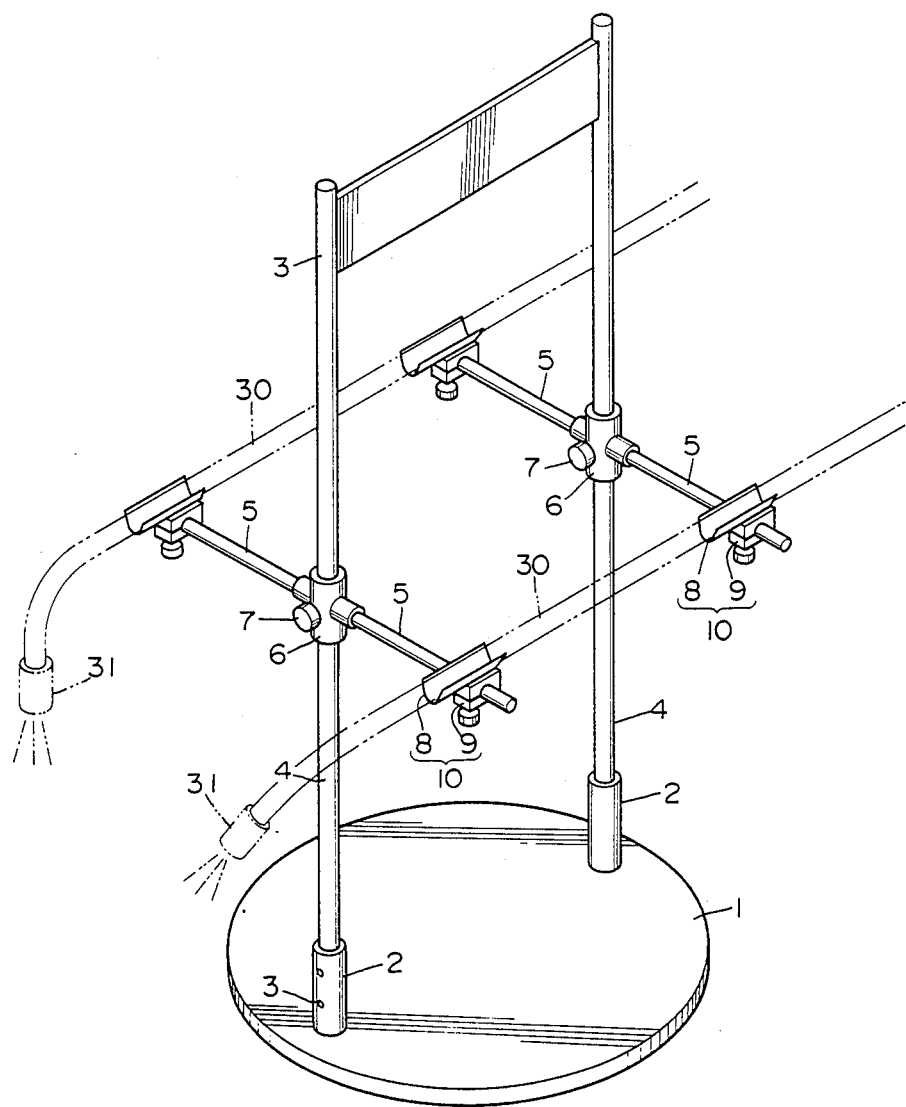
FIG. 1 is a perspective construction view for explaining an embodiment of an optical conductor cable supporting stand for use in a form of medical treatment as performed by light ray radiation according to the present invention.

FIG. 1 is a perspective construction view showing an embodiment of an optical conductor cable supporting stand according to the present invention. In FIG. 1, 1 is a fixed pedestal, and pipes 2 are fixedly mounted on a fixed pedestal 1 by welding or other bonding method. An upright pole 4 is inserted into the pipe 2 and fixedly attached thereto by means of a screw 3. A cable supporting arm 5 is fixedly connected with the upright pole 4 by means of a supporting fixture 6 so as to intersect the upright pole 4. The supporting fixture 6 is fixedly mounted onto the upright pole 4 by means of a set screw 7 with possible adjustability in an up-and-down direction and in a rotational direction.

On the other hand, both ends of the cable supporting arm 5 are inserted into a cable supporting fixture 10, and the latter 10 is moved slidably in the axis of the supporting arm and rotatably around the supporting axis fixedly connected with the supporting arm 5 by means of a fixing portion 9 of the supporting fixture 10. A cable-receiving portion 8 of the supporting member 10 is fixedly mounted on the fixing portion 9 thereof and employed for receiving the optical conductor cable 30. The cable receiving portion 8 is, for instance, V-shaped or semicircular. An optical conductor cable 30 is put on the cable receiving portion 8. Natural light rays corresponding to the visible light rays components of solar rays are guided into the optical conductor cable 30 from the light source not shown in FIG. 1. The light rays guided through the optical cable are radiated onto the diseased part of a patient from the light-emitting portion 31 located at the tip end of the optical conductor cable 30.

Figure 2A:
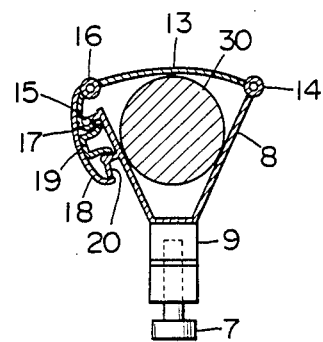
FIG. 2 (a)-(d) are views showing embodiments of a holding member 10 in FIG. 1.
Figure 2B:
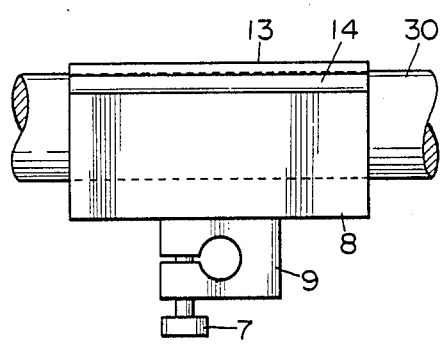

FIGS. 2a through 2d show another embodiment of the supporting member 10. FIG. 2a is a cross-sectional view thereof, and FIG. 2b is a side view of FIG. 2a. In order to more and more stably support the optical conductor cable 30, a pressing plate 13 rotating around the axis of a hinge 14, and pressing the optical conductor cable 30 onto the cable-receiving portion 8, is added to the cable-receiving portion 8.

The other end of the pressing plate 13 is fixed in such a manner that a hook 17 rotating around the axis of the hinge 16 is engaged with a pin 15 mounted on the other surface of the cable-receiving portion 8, a stop-plate 18 provided with a spring 19 therein is rotated around the axis of the hinge 16, and the spring 19 is inserted between a spring-receiving portion 20 and fixedly attached to the cable-receiving portion 8 and of the aforementioned hook 17.

Figure 2D:
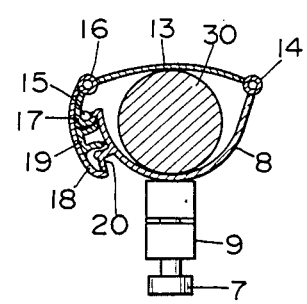
Figure 2C:
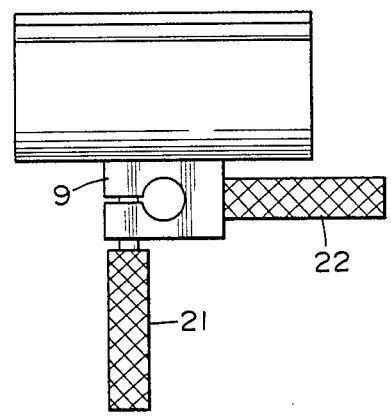

FIG. 2c shows a modification of this embodiment in which a handle 21 is added to the fixing portion 7, and further another handle 22 perpendicular thereto is provided for the purpose of easily turning the optical conductor cable 30 around the supporting arm 5. FIG. 2d shows another modification thereof in which the cross-section of the cable-receiving portion 8 is approximately semi-circular. Moreover, the number of holding members 10 per one upright pole 4 is not limited to one.

Figure 3:
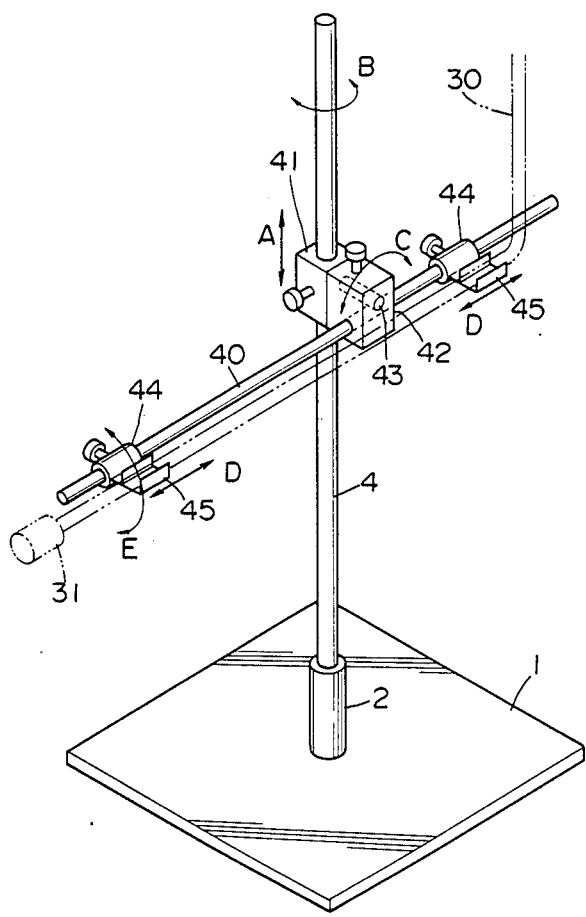
FIG. 3 is a perspective construction view for explaining the other embodiment of the supporting stand according to the present invention.

FIG. 3 is a perspective construction view for explaining still another embodiment of the present invention. In the embodiment, two receiving portions 45 for putting thereon the optical conductor cable 30 are mounted on a single, supporting arm 40 in order to stably hold the optical conductor cable 30. Namely, in FIG. 3, 41 is a fixing block mounted on the upright pole 4 which is capable of sliding in an up-and-down direction (shown by arrow A) and rotating in a circumferential direction (shown by arrow B), and a block 42 is attached to the block 41 through the shaft 43 and attached thereto in such a manner that the block 42 can rotate in a direction shown by arrow C. The afore-mentioned supporting arm 40 is inserted into the block 42 slidably in the axis direction and rotatably in the circumferential direction (direction C). Blocks 44 for putting thereon the optical conductor cable 30 are mounted on the supporting arm 40 at several places i.e. at least two places. Those blocks 44 can slide along the supporting arm 40 in the direction of the axis (direction D), and further those blocks 44 unitarily have a cable-receiving portion 45 for putting thereon the optical conductor cable 30.

Consequently, according to this embodiment, the optical conductor cable 30 can be supported at several places i. e. at least at two places by use of the single supporting arm 40, and therefore it may be possible to stably hold the optical conductor cable 30 in place. Furthermore, the height of the optical conductor cable is adjusted by moving the block 41 in an up-and-down direction, and the direction of the light-emitting end 31 thereof is adjusted by rotating the same in a circumferential direction. And further, the supporting arm 40 is rotated around the shaft 43, or the position of the block 44 to be fixed on the supporting arm 40 and the rotational angle thereof are changed. In such a manner, the direction of the light rays emitted from the light-emitting end 31 of the optical conductor cable 30 can be changed, and the optical conductor cable 30 can be stably held onto the cable-receiving portion 45.

Furthermore, when the incline of the supporting arm 40 is increased, there is a fear that the optical conductor cable 30 will slide onto the cable-receiving portion 45 slipping down therefrom. On that occasion, it may be preferable to fixedly mount the optical conductor cable 30 on the cable-receiving rest portion 45. For instance, the holding mechanism as shown in FIG. 2 can be preferably employed on the cable-receiving rest portion 45.

As is apparent from the foregoing description, the present invention has such characteristics that the visible light rays of solar rays or artificial light rays are effectively radiated onto a diseased part of a patient, and further the position of the light rays radiating onto the diseased part can be set easily and rapidly and the optical conductor cable, employed for radiating the light rays, can be easily moved, by the use of the cable support according to the present invention. And, In the case of employing two or more upright poles, the optical conductor cable 30 is held by two holding members 10 arranged at a predetermined interval, and therefore the same can be held more and more stably. Furthermore, the fine adjustment of the cable's position can be easily done by fixing one side of the cable and adjusting the position of another side thereof.

I claim:

1. A light ray radiation device for use in medical treatment comprising an elongated optical conductor cable for transmitting the visible light rays component of solar rays, said cable having a longitudinal end, a light emitting means on said longitudinal end for emitting said transmitted light rays on to a person's body, a supporting stand for supporting said optical conductor cable, said support stand comprising a pedestal, a plurality of spaced upright poles fixed to said pedestal, a support fixture slidably and rotatably mounted on each of said poles, a support arm fixed to each of said support fixtures and extending perpendicular to said poles, a cable support means slidably and rotatably mounted on each of said support arms, one of said cable support means receiving and engaging a first section of said cable, another of said cable support means receiving and engaging a second section of said cable, said first section being longitudinally spaced from said second section, whereby the position and orientation of said light emitting end on the longitudinal end of said cable can be varied by independently sliding and rotating either one of said support fixtures on its respective pole, by independently sliding and rotating either one of said cable support means on its respective support arm, and by sliding and rotating said cable in each of said cable support means.

2. A light ray radiation device according to claim 1, wherein each of said cable support means comprises a cable receiving member having a closed bottom part and side walls extending from said bottom part, said side walls being spaced from one another and extending generally upwardly from said bottom part, said side walls generally converging towards one another as said bottom part is approached, said cable being received between said side walls in a position overlying said bottom part, one of said side walls having an upper end, said cable support means further comprising a pressing plate, said cable supporting means further comprising a first hinge on said upper end of said one side wall for pivotably mounting said pressing plate between a closed pivotable position in which said pressing plate engages and presses said cable in said cable receiving member and another open pivotable position which enables said cable to be inserted and removed from said cable receiving member, said cable supporting means further comprising hook means for detachably connecting said pressing plate to said other side wall of said receiving member.

3. A light ray radiation device according to claim 2, wherein said hook means comprises a hook member, a second hinge pivotably mounting said hook member on said pressing plate, said other side wall of said receiving member having an upper end, a hook-engaging means mounted on said upper end of said other side wall, said hook member being pivotal to a hook-engaging position in which said hook member engages said hook-engaging means to cause said pressing plate to press said cable in said cable receiving member.

4. A light ray radiation device according to claim 3, wherein said hook means further comprises a stop plate pivotably mounted on said second hinge, a spring means on said stop plate, said other side wall of said receiving member having a spring-engaging means which is spaced from said hook-engaging means, said stop plate being pivotal to a closed position wherein said stop plate overlies said hook member and said spring means is resiliently received between said spring-engaging means and a hooked end part of said hook member when said hook member is in said hook-engaging position.

5. A light ray radiation device according to claim 4, wherein said hook-engaging means comprises a pin mounted on said upper end of said other side wall of said receiving member, said hooked end part engaging said pin when said hook member is in said hook-engaging position.

6. A light ray radiation device according to claim 5, wherein said spring means comprises a generally U-shaped member having a base and two spaced legs extending from said base, said base being fixed to said stop plate, said two spaced legs being resiliently retained between said spring-engaging means and said hooked end part when said hook member is in said hook-engaging position and said stop plate is in said closed position.

7. A light ray radiation device according to claim 1, wherein each of said cable support means has a generally V-shaped configuration.

8. A light ray radiation device according to claim 1, wherein each of said cable support means has a generally semicircular configuration.

9. A light ray radiation device according to claim 1 further comprising mutually perpendicular handles extending from said cable support means.

10. A light ray radiation device comprising an elongated optical conductor cable for transmitting the visible light ray component of solar rays, a supporting stand for supporting said optical conductor cable, said support stand comprising a pedestal, a plurality of spaced upright poles fixed to said pedestal, a support fixture slidably and rotatably mounted on said poles, a support arm fixed to said support fixtures and extending perpendicular to said poles, a cable support means slidably and rotatably mounted on each of said support arms, one of said cable support means receiving and engaging a first section of said cable, another of said cable support means receiving and engaging a second section of said cable, said first section being longitudinally spaced from said second section, whereby the position and orientation of said cable can be varied by independently sliding and rotating either one of said support fixtures on its respective pole, by independently sliding and rotating either one of said cable support means on its respective support arm, and by sliding and rotating said cable in each of said cable support means, each of said cable support means comprising a cable receiving member having a closed bottom part and side walls extending from said bottom part, said side walls being spaced from one another and extending generally upwardly from said bottom part, said side walls generally converging towards one another as said bottom part is approached, said cable being received between said side walls in a position overlying said bottom part, one of said side walls having an upper end, said cable support means further comprising a pressing plate, said cable supporting means further comprising a first hinge on said upper end of said one side wall for pivotably mounting said pressing plate between a closed pivotable position in which said pressing plate engages and presses said cable in said cable receiving member and another open pivotable position which enables said cable to be inserted and removed from said cable receiving member, said cable supporting means further comprising a hook means for detachably connecting said pressing plate to said other side wall of said receiving member, said hook means comprising a hook member, a second hinge pivotably mounting said hook member on said pressing plate, said other side wall of said receiving member having an upper end, a hook-engaging means mounted on said upper end of said other side wall, said hook member being pivotal to a hook-engaging position in which said hook member engages said hook-engaging means to cause said pressing plate to press said cable in said cable receiving member, said hook means further comprising a stop plate pivotably mounted on said second hinge, a spring means on said stop plate, said other side wall of said receiving member having a spring-engaging means which is spaced from said hook-engaging means, said stop plate being pivotal to a closed position wherein said stop plate overlies said hook member and said spring means is resiliently received between said spring-engaging means and a hooked end part of said hook member when said hook member is in said hook-engaging position.

11. A light ray radiation device according to claim 10, wherein said hook-engaging means comprises a pin mounted on said upper end of said other side of said receiving member, said hook member having a hooked end part which engages said pin when said hook member is in said hook-engaging position.

12. A light ray radiation device according to claim 11, wherein said spring means comprises a generally U-shaped member having a base and two spaced legs extending from said base, said base being fixed to said stop plate, said two spaced legs being resiliently retained between said spring-engaging means and said hooked end part when said hook member is in said hook-engaging position and said stop plate is in said closed position.

* * * * *